United States Patent

Porfano et al.

[11] Patent Number: 6,164,044
[45] Date of Patent: *Dec. 26, 2000

[54] METHOD AND APPARATUS FOR ASSEMBLING AND PACKAGING MEDICAL DEVICES

[75] Inventors: Donald J. Porfano, Hackensack, N.J.; James C. Kropatsch; Mark A. German, both of Columbus, Nebr.; Robert B. Odell, Franklin Lakes, N.J.

[73] Assignee: Becton Dickinson and Company, Franklin Lakes, N.J.

[*] Notice: This patent is subject to a terminal disclaimer.

[21] Appl. No.: 09/267,108

[22] Filed: Mar. 12, 1999

Related U.S. Application Data

[60] Provisional application No. 60/077,897, Mar. 13, 1998, and provisional application No. 60/102,338, Sep. 29, 1998.

[51] Int. Cl.[7] .............................. B65B 7/28; B65B 43/00; B65B 35/30
[52] U.S. Cl. ................................ 53/471; 53/489; 53/452; 53/443; 422/28
[58] Field of Search ............................ 53/425, 420, 452, 53/471, 489, 490, 443; 65/36; 141/1; 422/28

[56] References Cited

U.S. PATENT DOCUMENTS

4,521,237  6/1985  Logothetis ................................ 65/36
4,628,969  12/1986  Jurgens, Jr. et al. ....................... 141/1

*Primary Examiner*—Peter Vo
*Assistant Examiner*—Louis C. Huynh
*Attorney, Agent, or Firm*—Allen W. Wark

[57] ABSTRACT

A housing assembly is provided to define a locally controlled environment to maintain a localized clean work area without the need to maintain cleanliness levels in an entire room as in conventional clean rooms. The housing assembly includes a HEPA filter coupled to an air inlet to filter all of the air entering the housing. An air blower is coupled to the air inlet to feed filtered air into the housing assembly and to maintain a positive air pressure in the housing assembly to prevent unfiltered outside air from entering. Prefillable medical containers, such as syringe barrels and syringe tip closures, are introduced into the housing assembly where the syringe barrels and tip closures are cleaned with filtered ionized air and the tip closures are coupled to the barrels. A thin coating of a lubricant is applied to the inner surface of each of the syringe barrels. The syringe barrels can be filled with a substance. Alternatively, while still in the housing assembly the syringe barrels can be formed into an array and placed in a clean container. A cover is then attached to the tub to completely enclose the array of syringe barrels followed by an outer wrap. Thereafter, the syringe barrels either filled or packaged in the array can be sterilized. The syringe barrels may be prefillable plastic syringe barrels made of a cyclic polyolefin copolymer or polypropylene.

44 Claims, 8 Drawing Sheets

METHOD AND APPARATUS FOR ASSEMBLING AND PACKAGING MEDICAL DEVICES

CROSS-REFERENCE TO RELATED APPLICATION

This application claims the benefit under 35 U.S.C. §119 (e) of U.S. provisional application Ser. No. 60/077,897 filed Mar. 13, 1998 and U.S. provisional application Ser. No. 60/102,338 filed Sep. 29, 1998, which are hereby incorporated by reference in their entirety.

FIELD OF THE INVENTION

The present invention relates generally to a method of partially assembling and packaging medical devices, such as syringe components and in particular prefillable syringe barrels in a clean, substantially particulate-free area. More particularly, the invention is directed to a method for assembling, filling and packaging medical devices in a locally controlled environment which is clean and substantially free of airborne particulates.

BACKGROUND OF THE INVENTION

Syringes have been classified into several general types. The first type is assembled and placed in sterile packaging which can be shipped with a vial or ampoule of a drug or other injectable solution. The vial or ampoule is generally made of glass or other clear material that does not interfere with the stability of the drug during prolonged storage. The syringe is filled with the drug or other solution at the point of use and injected into the patient. Another type of syringe is packaged with a vial filled with a powdered or lyophilized drug which is dissolved in water or other suitable solvent prior to charging into the syringe.

These syringes have the disadvantage of increasing the time and difficulty of filling the syringe at the point of use with increased possibility of contamination of the syringe and/or drug solution. There is a further risk of glass particles from the ampoules contaminating the drug solution when the ampoules are opened.

Several of these disadvantages of syringes are overcome by providing prefilled syringes which can be filled with a suitable drug solution prior to use. Prefilled syringes as the term is known in the art are syringes that are filled by the drug manufacturer and shipped to the health care provider ready for use. The prefilled syringes have the advantage of convenience and ease of application with reduced risk of contamination of the drug solution. A difficulty in producing prefilled syringes, if they are made of plastic rather than glass, is selecting suitable materials that maintain their clarity for extended periods of time and do not contaminate or react with the drug solution.

Syringes and other medical appliances are generally produced and packaged in clean rooms to maintain proper cleanliness levels. The clean rooms are equipped with extensive filter assemblies and air control systems to remove particulates and pyrogens from the air in the room and to prevent particulates and pyrogens from entering the room. The operators and other personnel in the clean room are required to wear appropriate protective garments to reduce contamination of the air and the medical appliances being manufactured or assembled. As people and equipment enter and leave the clean room the risk of contamination and introduction of foreign particulates and pyrogens increases.

Accordingly, there is a continuing need in the industry for an improved system for manufacturing and assembling clean and sterile medical devices, as well as such filling devices, without the complexity and expense associated with clean rooms.

SUMMARY OF THE INVENTION

The present invention is directed to a method and apparatus for maintaining a clean environment for various assembly operations for medical devices and medical appliances. More specifically, the invention is directed to the use of a locally controlled environment for maintaining cleanliness levels for assembling medical devices, without the need for clean rooms. The medical devices can be filled with a suitable substance such as water, saline solutions, flush solutions, contrast agents, pharmaceutical agents, and vaccines in either a dry or liquid state.

Accordingly, a primary object of the invention is to provide at least one housing assembly to define a locally controlled environment for receiving medical devices or components where the components can be assembled within the housing assembly under controlled conditions.

Another object of the invention is to provide a method for assembling a syringe barrel and tip closure in a locally controlled environment.

A further object of the invention is to provide a method for filling a medical container, such as a syringe barrel, in a locally controlled environment.

A further object of the invention is to provide a method for assembling an array of medical containers, such as syringe barrels in a tray and packaging the array in a container while in a locally controlled environment.

A still further object of the invention is to provide a method for assembling tip closures to prefillable plastic syringe barrels in a locally controlled environment.

Another object of the invention is to provide a housing assembly to define a locally controlled environment where the housing assembly includes a HEPA filter and an air blower assembly to feed filtered air into the housing and maintain the housing assembly at predetermined cleanliness levels.

A further object of the invention is to provide a housing assembly to define a locally controlled environment for packaging an array of syringe barrels in closed containers and thereafter sterilizing the syringe barrels in the closed container.

The housing assembly defining the locally controlled environment can be a portable unit having a work surface for performing the desired operations manually or automatically. The work surface is enclosed by side panels which are preferably transparent to allow viewing by an operator. The assembly includes a top wall coupled to the side panels to define an enclosure. The top wall includes a fan or blower assembly and a filter assembly to direct filtered air into the housing and maintain a clean environment. The blower assembly can be operated to maintain a positive pressure in the housing assembly to prevent the infiltration of unfiltered air. An optional exhaust fan can also be provided to draw air downwardly through the housing assembly and exhaust the air without causing a negative pressure in the housing assembly.

Medical containers such as syringe barrels are placed in the housing assembly where they are cleaned by streams of clean filtered air or ionized air. The clean air removes substantially all particulates that are adhered to the inner and outer surfaces of a syringe barrel to attain the desired cleanliness level. A vacuum can be provided in the area of the barrel to carry the particulates away from the barrel and out of the housing assembly. Tip closures or syringe needles with their associated needle sheaths are also supplied to the housing assembly where they can be cleaned with filtered air or ionized air. The tip closure is coupled to the syringe barrels. A lubricant is then applied to the inner surface of the syringe barrel, and the syringe barrels are placed in a grid or tray which then is placed in a container such as a tub. A plastic sheet is placed over the tray and the tub is closed with a sheet of flexible material which generally is heat sealed to the tub. The tub is then enclosed in an outer wrap such as a plastic bag which is heat sealed. The tub, outer wrap and contents are sterilized by a sterilizing gas or radiation. These operations can be conducted in a single housing assembly or in a plurality of housing assemblies coupled together.

A method of producing a prefillable syringe in accordance with the present invention comprises the steps of supplying a plurality of syringe barrels to a first housing assembly having an air filtering device to maintain a predetermined cleanliness level therein, supplying a plurality of tip closures to the first housing assembly and assembling the tip closure on the syringe barrels. A stream of filtered air is directed to the syringe barrels and tip closures to remove particulates therefrom and clean the outer surfaces thereof. The syringe barrels and tip closures are conveyed to a second housing assembly having a filtering device for maintaining a predetermined cleanliness level, cleaning the inner surface of the syringe barrel, and applying a lubricant to an inner surface of the syringe barrels. In a third housing assembly, the syringe barrels and tip closures are formed into an array and placed into a container having a closed bottom, side walls and an open top. Thereafter, the container is conveyed to a fourth housing assembly having an air filtering device to maintain a predetermined cleanliness level, and a closure is applied to the container to seal the container.

Prefilled medical containers, such as syringes, can be produced by supplying syringe barrels and a closure to an environmentally controlling housing assembly where the components are cleaned and the barrel preferably lubricated. The closure can be a tip cap or stopper to close one end of the syringe barrel, the barrel filled with a drug and closed to form a prefilled syringe. Thereafter, the prefilled syringe barrels are packaged and sterilized. Each step can be performed in a single housing assembly or transferred to a subsequent housing assembly.

The aspects of the invention are further attained by providing a method of producing a filled syringe comprising the steps of: forming a plastic syringe barrel in an injection molding machine, the syringe barrel having a cylindrical side wall, an open proximal receiving end and a frustoconically shaped outlet nozzle at its distal end and transferring the syringe barrel, without any additional cleaning or sterilization, into an environmentally controlled area to maintain a predetermined cleanliness level. A stream of filtered air is directed toward the syringe barrel in the environmentally controlled area to remove particles from surfaces thereof to clean the syringe barrel. A stopper is delivered to the environmentally controlled area and inserted into the open proximal end of the syringe barrel to close said proximal end. The syringe barrel is filled with a substance through its outlet nozzle. A tip cap is delivered to the environmentally controlled area, air cleaned in said environmentally controlled area, and assembled to the outlet nozzle of said syringe barrel to form a prefilled syringe. The prefilled syringe is then removed from the environmentally controlled area. Alternatively, a stopper is inserted into the open proximal end of the syringe barrel, followed by filling the syringe barrel through the outlet nozzle and then applying a cleaned tip cap to form a prefilled syringe.

These and other aspects, advantages and salient features of the invention will become apparent to one skilled in the art from the annexed drawings and the following detailed description which discloses preferred embodiments of the invention.

BRIEF DESCRIPTION OF THE DRAWINGS

Referring to the drawings which form a part of this original disclosure.

DETAILED DESCRIPTION OF THE INVENTION

The present invention is directed to a method and apparatus for assembling and packaging various medical containers, in clean, locally controlled environments. As used herein, medical containers for containing and/or dispensing substances include vials and injection devices, such as syringes. In addition, as used herein, substances include, for example, water, flush solutions and contrasting agents, saline solutions, pharmaceutical agents, and vaccines, either in a dry state or a liquid state. Although embodiments of the invention are disclosed as a hypodermic syringe assembly, it is within the purview of the present invention to include various other medical containers, such as plastic or glass cylindrical reservoirs having resilient stoppers and/or closures at one or both ends or other medical devices or appliances which require a clean environment during assembly or packaging.

Figure 1A:
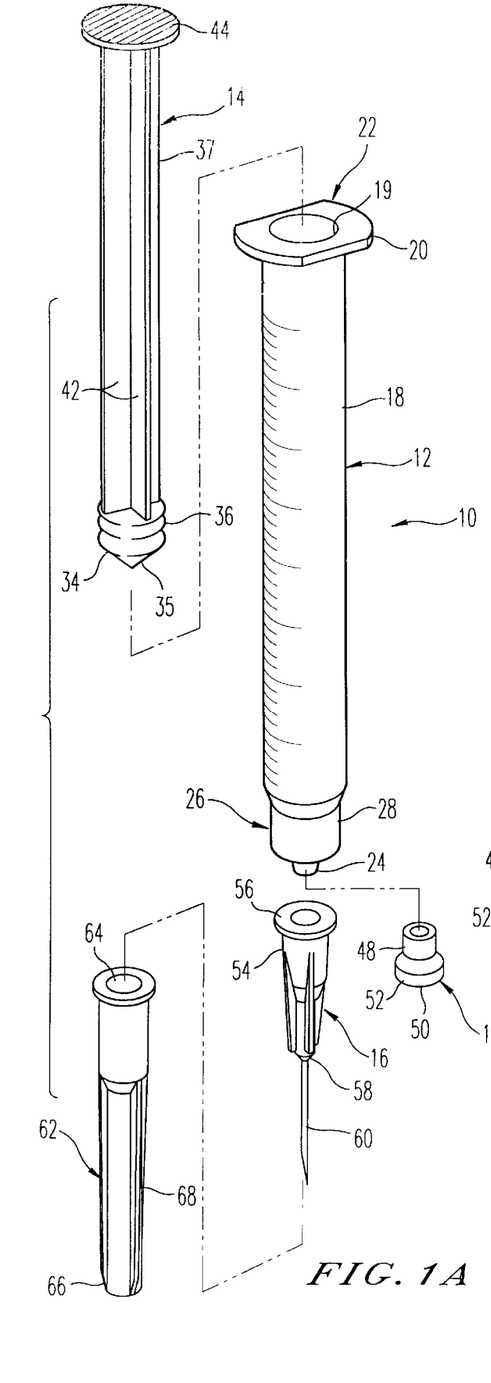
FIG. 1A is an exploded side view of a syringe.
Figure 1B:
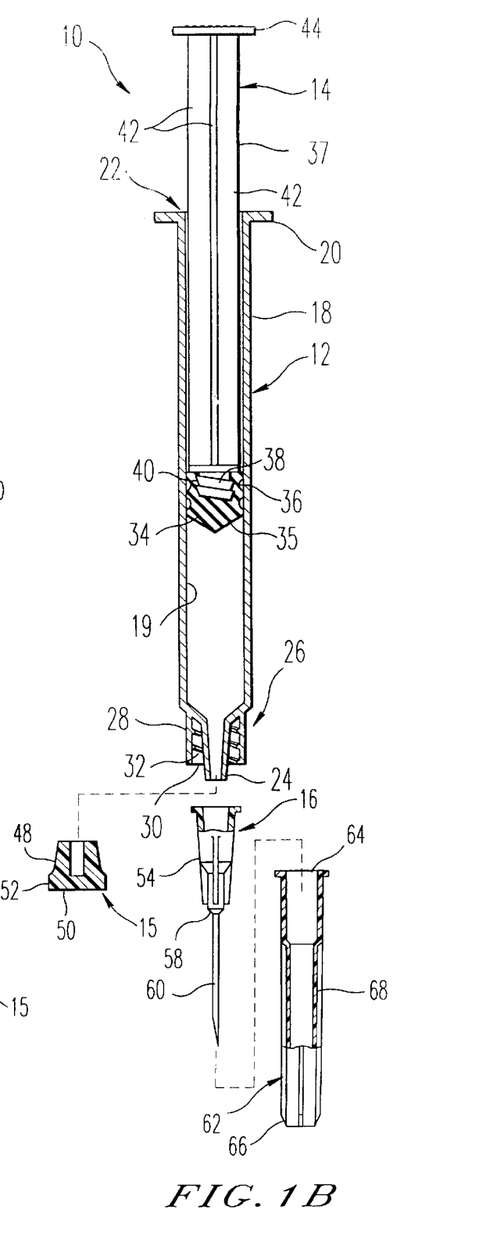
FIG. 1B is an exploded side view of a syringe shown in partial cross-section.

FIGS. 1A and 1B illustrate one embodiment where the medical container is a syringe 10 including a plastic syringe barrel 12, a plastic plunger 14 and a plastic tip closure 15 or needle tip closure 16. In further embodiments, syringe 10 can be a needleless syringe or a pen injector as known in the art. Syringe barrel 12 has a cylindrical side wall 18, a flange 20 at a receiving end 22, and a frustoconical outlet nozzle 24 at a discharge end 26. Collar 28 encircles the outlet nozzle 24 to define an annular space 30 surrounding the outlet nozzle 24. An inner surface of collar 28 includes a threaded portion 32. Side wall 18 can include suitable printed indicia for indicating the volume of the syringe, the name of the manufacturer and the like.

Although the syringe barrel illustrated in this embodiment includes a locking luer type collar, it is within the purview of the present invention to include syringe barrels without a collar, syringe barrels having an eccentrically positioned nozzle, and various other nozzle-like structures adapted to accept, either permanently or removably, a needle cannula or needle cannula assembly. It is only required that there is an aperture on the distal end of the syringe barrel in fluid communication with the interior of the syringe barrel. In addition to the tip closure and needle closure illustrated in this embodiment, it is also within the purview of the present invention to include a wide variety of closures for sealing a syringe barrel or drug container including, but not limited to, cannula occluding plugs, removable seals attached by adhesive or heat sealing, threaded closures and the like.

Plunger 14 includes a stopper 34 having a frustoconical end face 35, and a plurality of annular ridges 36 dimensioned to form fluid tight contact with the inner surface 19 of side wall 18 of syringe barrel 12. Stopper 34 is a molded flexible material, such as rubber, that is sufficiently pliable and flexible to readily conform to the inner surface 19 of the side wall 18. A plunger rod 37 is coupled to stopper 34 at a distal end by a suitable structure. In the embodiment shown in FIG. 1, plunger rod 37 includes in threaded member 38 which is coupled to an internally threaded recess 40 in stopper 34. Plunger rod 36 has four vanes 42 extending outwardly from a center longitudinal axis and extending at substantially right angles to each other. The plunger rod 37 terminates at a flat plate 44 for pushing the plunger rod 37 through syringe barrel 12.

Tip closure 15 is dimensioned to close the frustoconical nozzle 24 of syringe barrel 12. Referring to FIG. 1A, tip closure 15 has a slight frustoconical sleeve 48 with a closed end 50 and an outer annual flange 52. Sleeve 48 is dimensioned to fit securely over frustoconical nozzle 24. Tip closure 15 is typically made from flexible plastic or rubber-like materials, rigid plastic materials or peelable strip materials as known in the art.

Referring to FIG. 1A, needle tip closure 16 includes a sleeve 54 having a first end 56 for coupling to the frustoconical nozzle 24 of syringe barrel 12. A second end 58 of sleeve 54 receives a hollow stainless steel injector needle 60. A protective sheath 62 made of plastic has an open end 64 for coupling with sleeve 54 and a closed end 66 opposite open end 64. Protective sheath 62 has a hollow, substantially cylindrical shape and can be dimensioned to receive needle 60 with the side walls 68 being spaced from needle 60 so that sheath 62 does not contact needle 60. In alternative embodiments, sheath 62 can contact and close off the tip of needle 60.

The syringe of FIGS. 1A and 1B can be assembled by the manufacturer and packaged in suitable clean and sterile packaging. The syringes are typically packaged individually or in bulk. In embodiments of the invention, the syringe components can be partially assembled for producing pre-filled syringes by the customer, such as a pharmaceutical manufacturer or contract filler. A primary aspect of the invention is to provide a method of producing bulk packaging of syringe components for filling with a substance and the assembly of the plunger, syringe barrel and tip closure.

Figure 2:
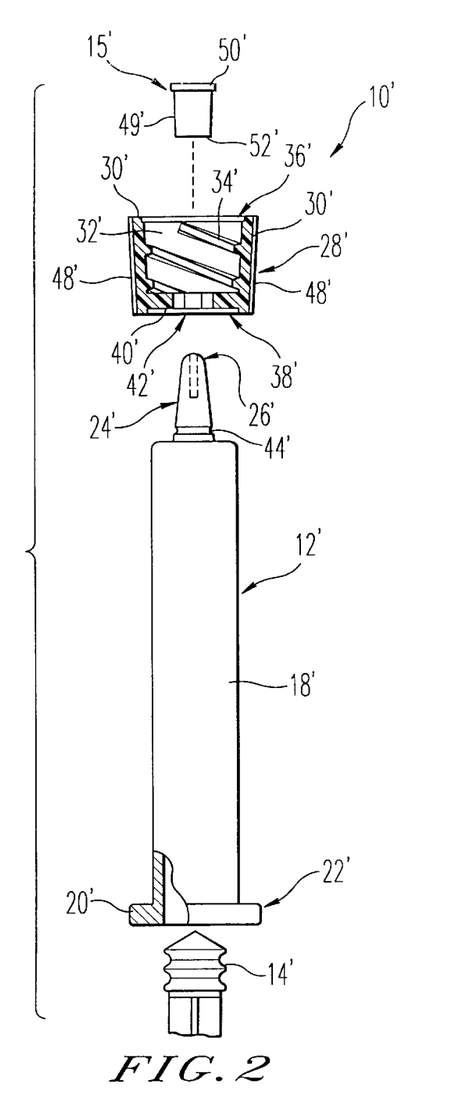
FIG. 2 is an exploded side view of a syringe in a further embodiment.

In a further embodiment shown in FIG. 2, syringe 10' includes a glass syringe barrel 12', a plastic plunger rod and attached rubber stopper or piston 14' and a tip closure 15' or needle sheath closure (not shown). In further embodiments, the syringe can be a needleless syringe as known in the art. Syringe barrel 12' in the embodiment illustrated has a cylindrical side wall 18', a flange 20' at a receiving end 22', and a frustoconical outlet nozzle 24' at a discharge end of a barrel tip 26'. A Luer locking collar 28' encircles the outlet nozzle 24' to define an annular space 30' surrounding the outlet nozzle 24'. Side wall 18' can include suitable printed indicia for indicating the volume of the syringe, the name of the manufacturer and the like.

Figure 3:
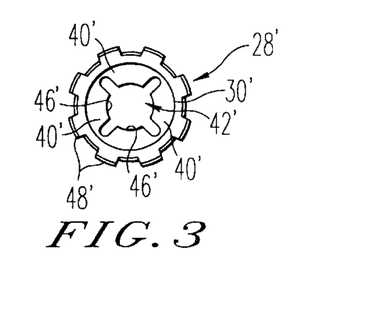
FIG. 3 is a top view of the luer locking collar of the syringe of FIG. 2.

Luer locking collar 28' is generally a plastic collar that is able to be snapped onto the nozzle 24' of the syringe barrel tip 26'. As shown in FIGS. 2 and 3, Luer locking collar 28' includes an annular sleeve 30' having an inner wall 32' with internal threads 34'. The annular sleeve 30' has an open end 36' for coupling with an externally threaded member. The sleeve 30' further has a base end 38' with a plurality of flexible tabs 40' extending radially inwardly toward the center axis of the sleeve 30' to define an opening 42'. The tabs 40' are sufficiently flexible to deflect out of the plane of the tabs along an axial direction to snap into a recess 44' on the tip 26' of the syringe barrel 12'. In the embodiment illustrated, four tabs 40' are included which are spaced apart around the sleeve 30' by radial gaps. The inner edges 46' of the tabs 40' have an arcuate shape complimenting the shape of the syringe barrel tip 26'. The outer surface of the sleeve 30' includes longitudinal ribs 48' for gripping and rotating the Luer locking collar 28' with respect to the syringe barrel 12'.

Syringe barrels 12 in accordance with the invention are manufactured using conventional plastic or glass molding techniques. The syringe barrels and other components can be manufactured using molding techniques that produce sterile components or components having a low bio-burden which are then supplied directly into the housing assembly to avoid contamination.

In embodiments, the syringes are prefillable syringes as known in the art having an internal volume of about 0.3–60 ml. The syringe barrels 12 are made of glass or of a plastic material suitable for long term storage of a substance. Examples of a suitable plastic materials include polyolefins, such as polypropylene, which can contain a clarifying agent. Other suitable polymer resins include cyclic olefin copolymers. The cyclic olefin copolymers as known in the art typically do not require a clarifying agent.

Figure 4A:
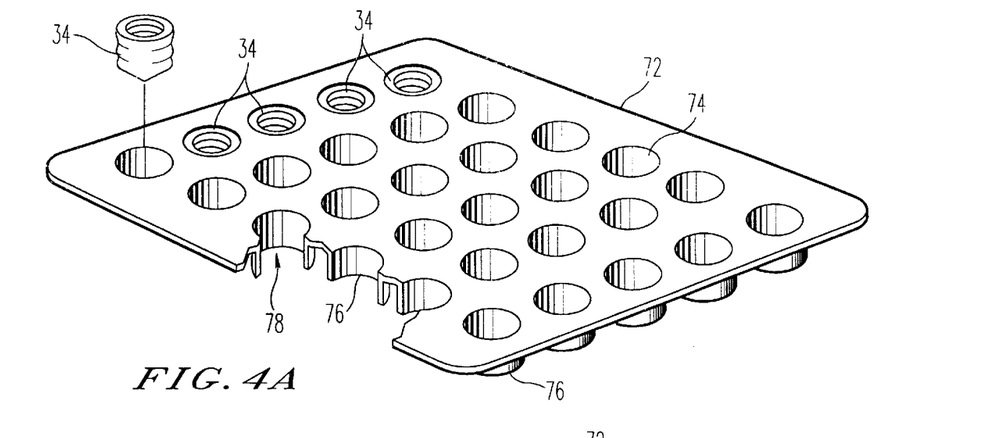
FIG. 4A is a perspective view of a tray for holding a plurality of stoppers.
Figure 4B:
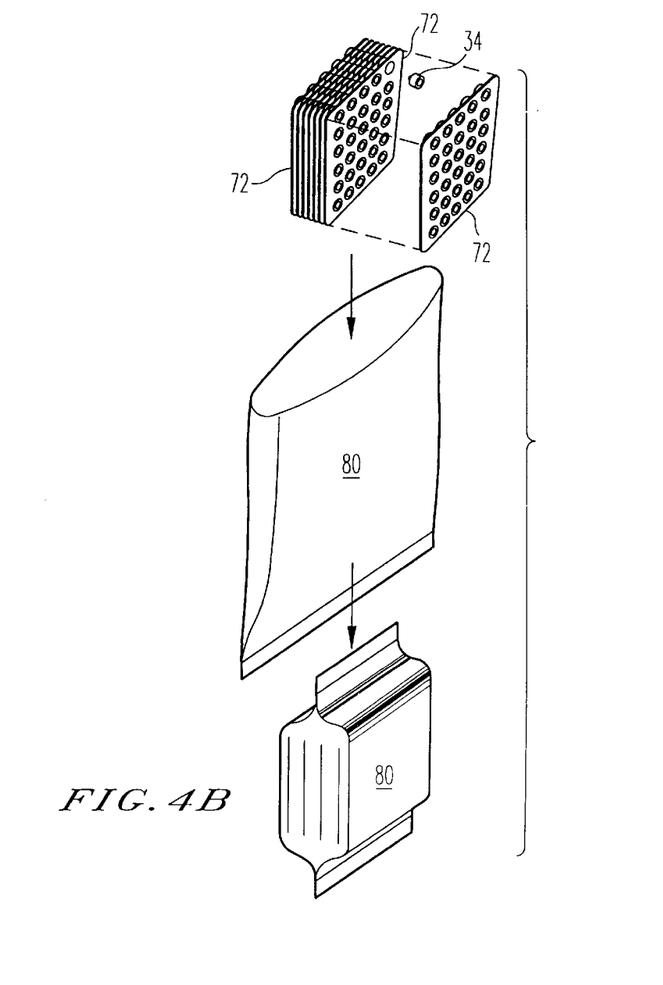
FIG. 4B is a schematic view of a stack of trays for the stoppers packaged in a plastic bag.

Referring to FIG. 4A, the stoppers 34 for the syringe plunger 14 are packaged in grid or tray 72 having a plurality of openings 74 and a slightly tapered, frustoconical shaped collar 76 around each opening 74. The collars 76 are dimensioned to receive the stoppers 34 so that the stoppers 34 nest in the openings 74. Collars 76 have an open end 78 so that the stoppers 34 can be easily removed by pushing downward through the open end 78. A plurality of trays 72 are stacked together to form a bulk package as shown in FIG. 4B. The end of collars 76 are able to fit into the opening 74 when stacked without contacting the stoppers 34. In embodiments of the invention, several of the trays 72 are stacked together to define a nested matrix and sealed in a plastic bag 80 or other protective outer wrap as shown in FIG. 2B. The stoppers 34 are preferably cleaned and lubricated before placing in the tray 72. The stoppers 34 can be sterilized before or after packaging in the plastic bag 80 or other outer wrap. In further embodiments, the stoppers 34 can be packaged in a second outer plastic bag or outer wrap.

Figure 5:
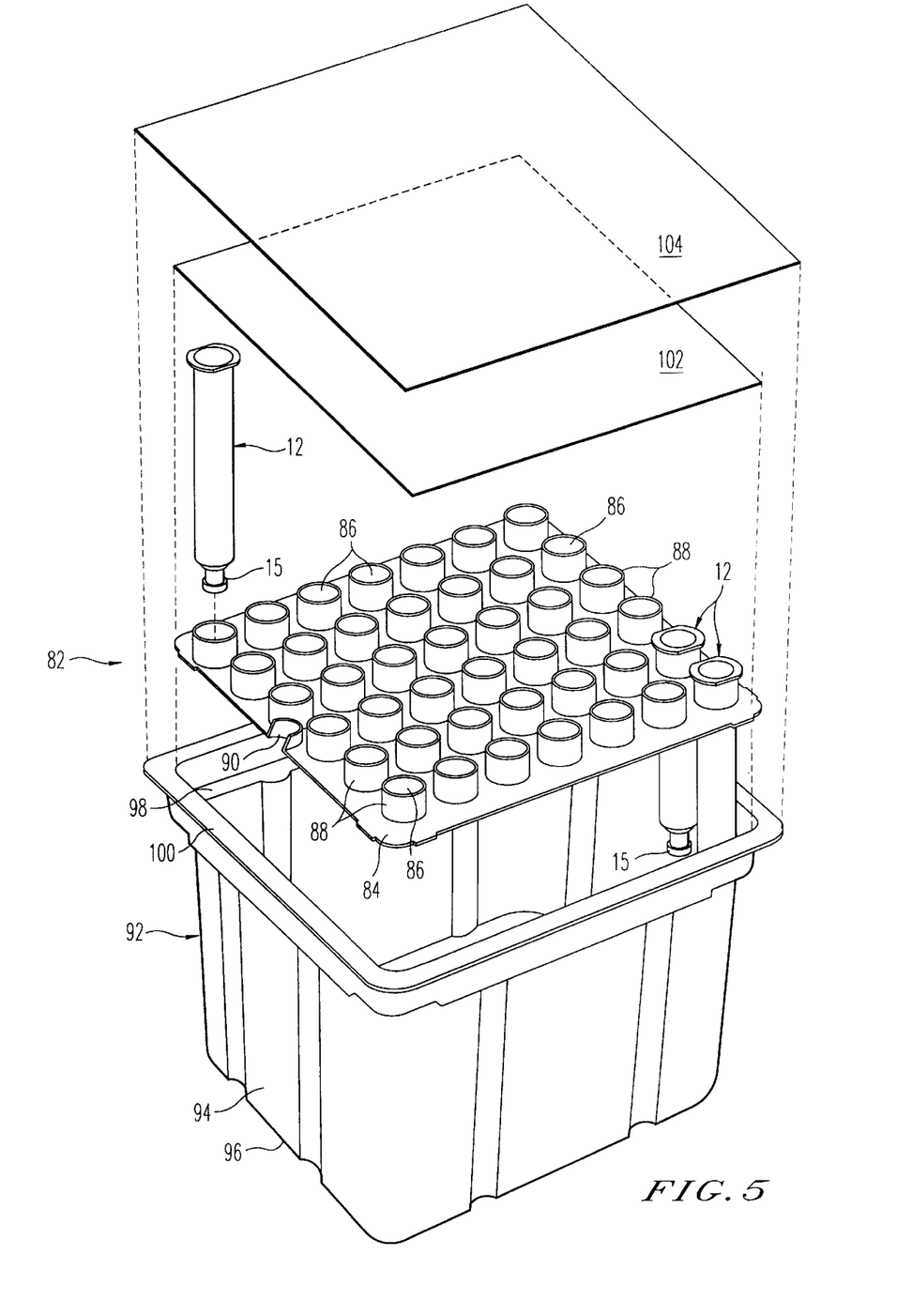
FIG. 5 is an exploded perspective view of a syringe barrel tub container in a preferred embodiment of the invention.

Referring to FIG. 5, a plurality of syringe barrel assemblies are placed in a container or tub package 82. The syringe barrel assemblies can be placed in any suitable package or container depending on the particular syringe and its end use. A tray 84 is provided having a plurality of spaced apart openings 86 and collars 88 extending upward for supporting the syringe barrels 12. In the embodiment illustrated, openings 86 and collars 88 are arranged in a series of rows and columns and are uniformly spaced apart. Tray 84 includes cut-out portions 90 for lifting and easily gripping the tray 84 and to orient the tray in various processing operations and filling locations. Tray 84 is nested in a suitable container such as a tub 92. Tub 92 includes side walls 94 and a bottom wall 96. A stepped portion 98 of tub 92 is formed in side walls 96 to support tray 84 so that the ends of syringe barrels 12 can be spaced from bottom wall 96. In embodiments of the invention, the ends of syringe barrels can contact bottom wall 96. A peripheral flange 100 extends outward from the open top end of side walls 94. Tub 92 is typically an integrally formed rigid plastic unit formed by a suitable molding process, such as, injection molding, vacuum forming or blow molding.

Tray 84 supports an array of syringe barrels 12 and is positioned in tub 92. A protective layer of sheet material 102, such as polyethylene or other plastic, is positioned to cover tray 84 and the syringe barrels 12. In embodiments of the invention, sheet 102 is substantially the same size as tray 84. A closure or cover sheet 104 is then positioned on peripheral flange 100 and sealed to completely enclose the array of syringe barrels 12. The tub 92 is then enclosed in a sealed plastic bag or wrapper. Typically, the cover sheet 104 is a thermoplastic material that is heat sealed to flange 100 to form a complete seal. A suitable cover sheet 104 is a gas permeable material such as a spun bonded polyolefin sold under the trademark TYVEK by E. I. DuPont & Co. This allows the syringe barrels 18 to be gas sterilized, if desired, while they are in the sealed tub 92.

The package 82 of syringe barrel assemblies and the packaged stoppers 34 are generally shipped to the customer along with the other necessary components to assemble a prefilled syringe. Each syringe barrel is filled with a predetermined amount of a drug solution while held in a closed, clean containment area. The containment area is then evacuated and the plunger is positioned in the open end of the syringe barrel. The vacuum is then released and the plunger is drawn into the syringe barrel by the vacuum formed within the barrel. In further embodiments, the plunger and syringe barrel can be assembled by a vent tube stoppering process as known in the art. Thereafter, the assembled syringes are packaged as prefilled syringes for use by the health care provider.

Figure 6:
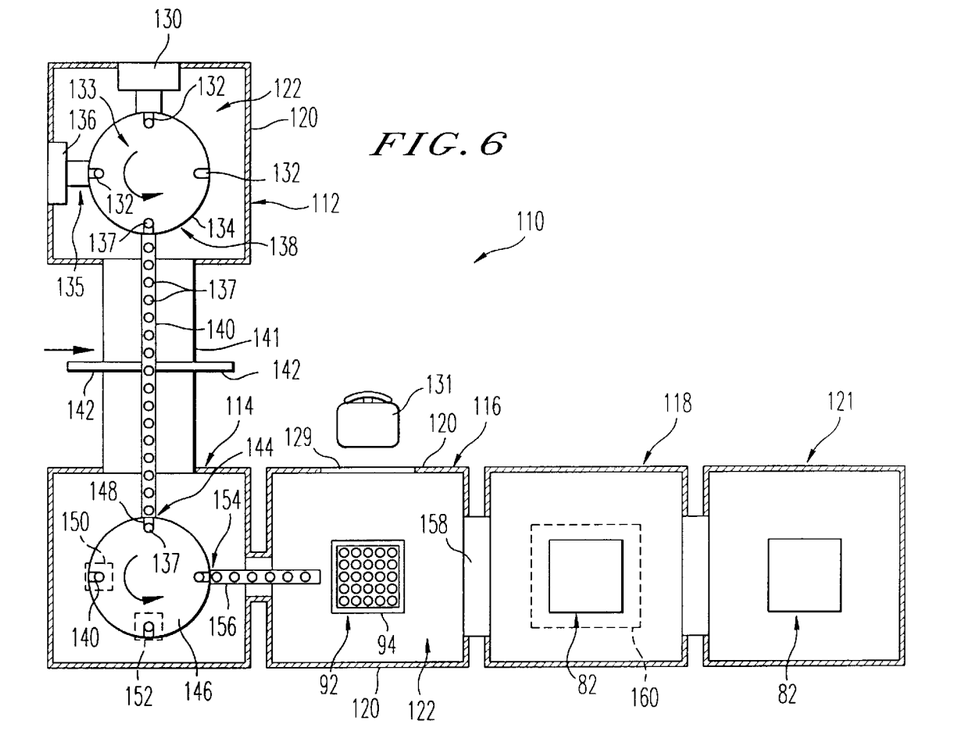
FIG. 6 is a perspective top view of a locally controlled environment for cleaning, assembling and packaging syringe barrels.
Figure 7:
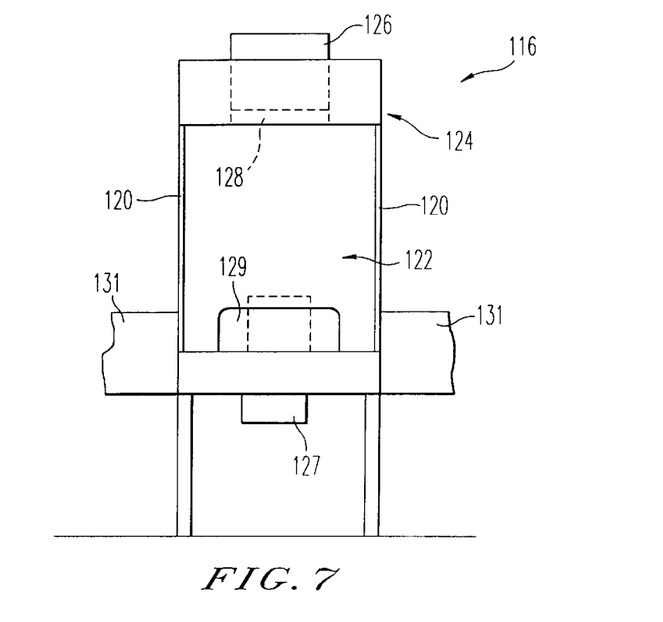
FIG. 7 is a side view of a housing assembly for providing a locally controlled environment.
Figure 8:
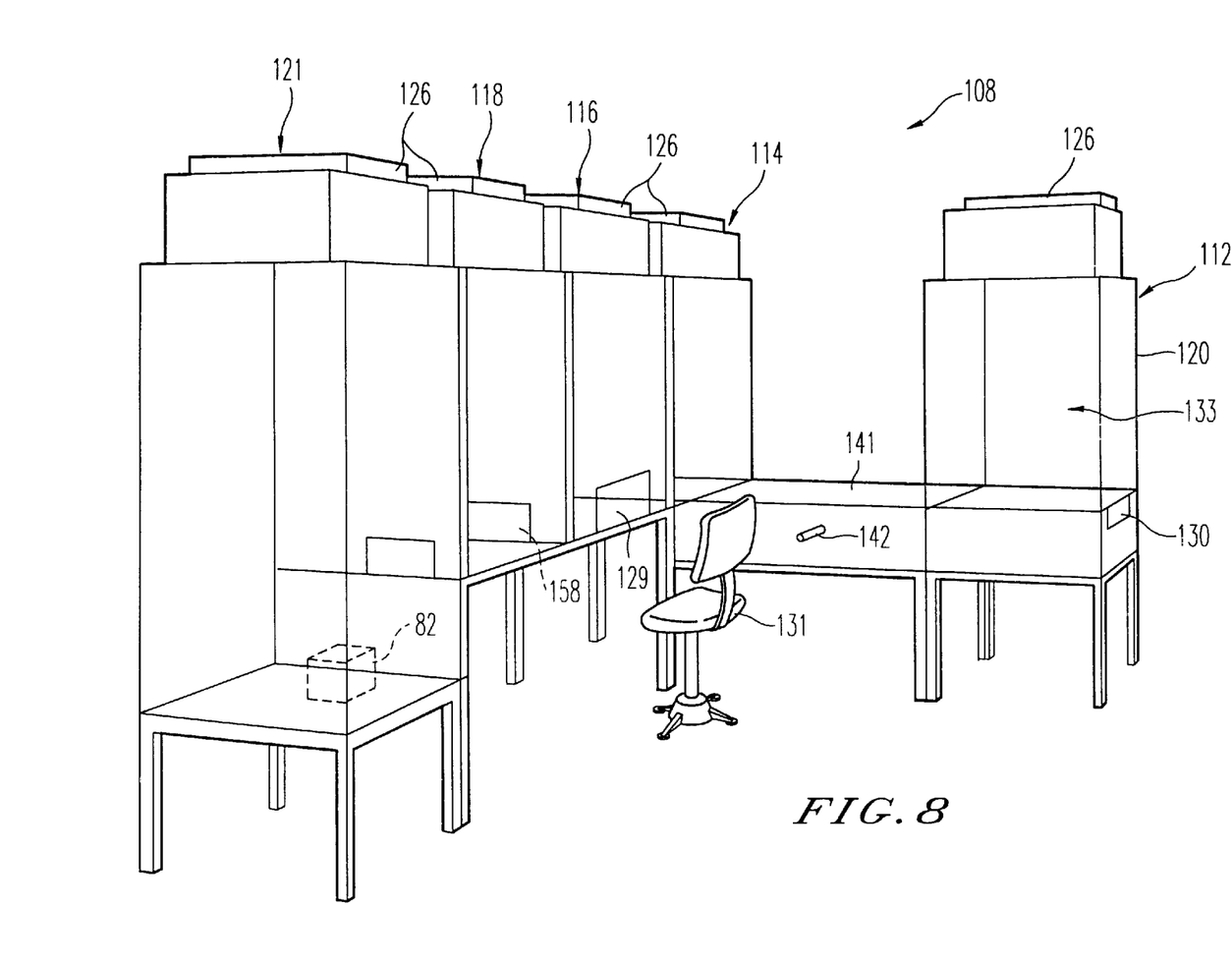
FIG. 8 is a perspective view of a locally controlled environment.
Figure 9:
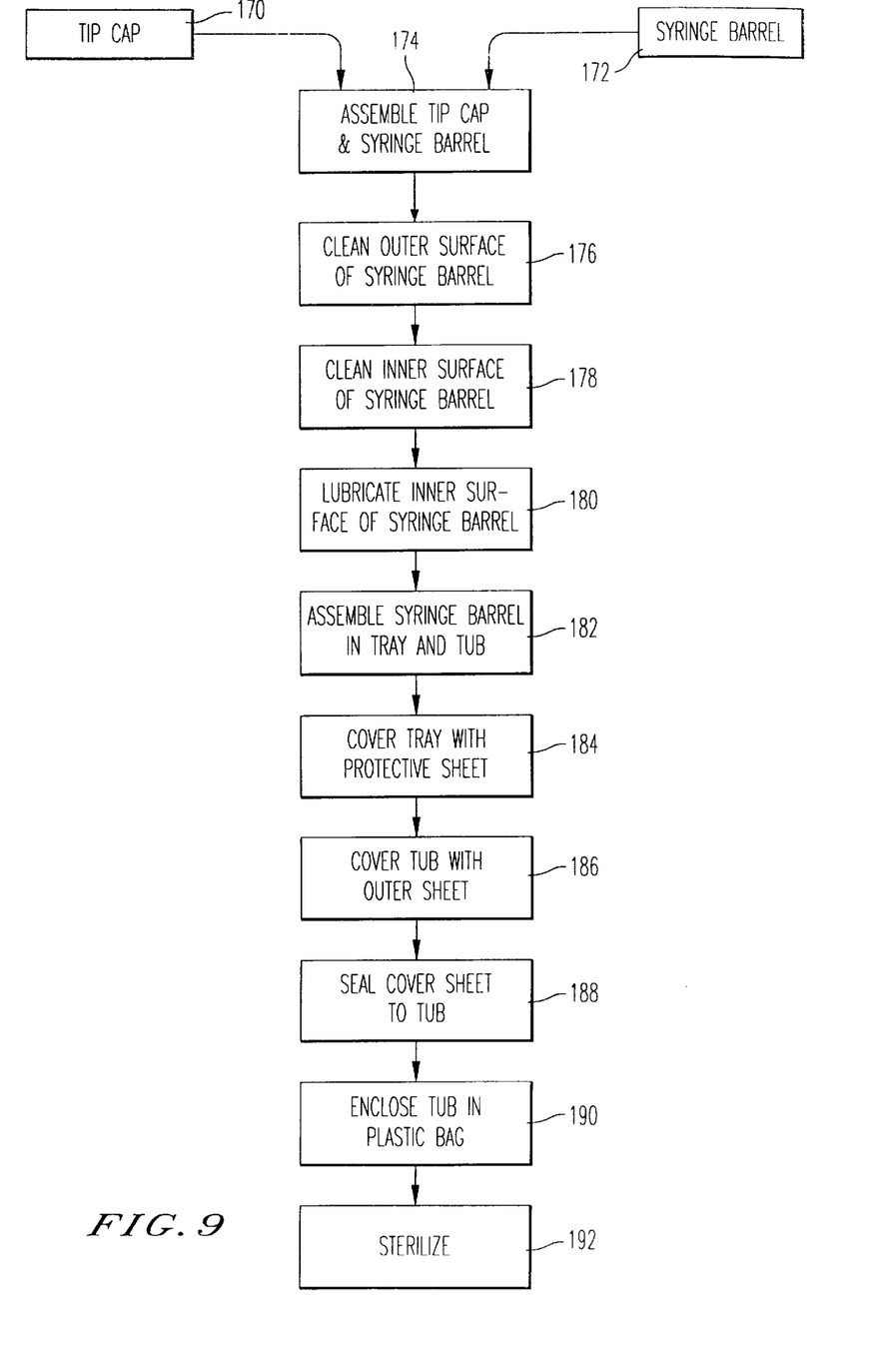
FIG. 9 is a schematic diagram of a flow chart of the assembly steps of packaged syringe barrel assemblies.

The barrel assembly tub package 84 is produced using an apparatus 110 depicted in FIGS. 6, 7 and 8 by the method outlined in the flow chart of FIG. 9. The apparatus 110 in the embodiment shown includes several modular housing assemblies 112, 114, 116 and 118 which are coupled together. Preferably, the housing assemblies are modular so that they can be separated from one another for repair or replacement. In addition, modular assemblies permit expansion or reduction in overall size to accommodate the particular needs of the overall operation. The modular housing assemblies can be coupled together directly or by an intermediate housing or tunnel to prevent infiltration of unfiltered air.

The housing assemblies are substantially alike, although they can differ in size or shape to accommodate the specific assembly step being performed. For purposes of illustration, housing assembly 116 is shown in FIG. 7 which includes side walls 120, some or all of which may be made of glass or other transparent materials, completely surrounding a work space 122. It will be appreciated that housing assemblies 112, 114, 116 and 118 are substantially similar and that FIG. 7 is intended to be illustrative of the housing assemblies. A top member 124 is coupled to side walls 120 to enclose work space 122. Top member 124 has an air blower 126 and is coupled to a high efficiency particulate air filter (HEPA) 128 to direct filtered air into the housing assembly. Preferably, air blowers 126 maintain a positive pressure in work space 122 to prevent infiltration of contaminated air. The efficiency of the HEPA filters determines the level of particulates and viable and non-viable particulates and pyrogens in the air in the work space 122. In embodiments of the invention, filter 128 removes particles of 0.3 microns or larger. In further embodiments, particles smaller than 0.3 microns can be removed.

In one embodiment of the invention, the HEPA filters are selected to maintain the housing assembly and the respective work space therein at levels meeting or exceeding Class 100 conditions with respect to particulates as defined by Federal Standard No. 209E, "Airborne Particulate Cleanliness Classes in Clean Rooms and Clean Zones", approved by the General Services Administration (Sep. 11, 1992). In further embodiments, the HEPA filters are selected to maintain high cleanliness standards as needed which can be higher or lower than Class 100.

Air blower 126 directs clean filtered air downward through the housing assembly to an outlet (not shown) in the lower end of the housing assembly. An optional exhaust fan 127 can be included to draw air and any particulates or other contaminants out of the housing assembly. One or more of the side walls 120 can include an optional access opening 129 to enable an operator to reach into the workspace and perform various operations. As shown in FIG. 6, a chair 131 or stool is provided for the operator. A positive pressure is preferably maintained in the workspace 122 to prevent air from entering through access opening 129.

The housing assembly 116 shown in FIG. 7 is coupled to an adjacent housing assembly in a manner to maintain a clean locally controlled environment. As shown, a tunnel-like enclosure 131 is attached to the side walls 120 to carry the workpiece, such as a medical device, from one housing assembly to another without exposure to outside air. An air blower and appropriate HEPA filter can be provided in enclosure 131 as needed to maintain desired cleanliness levels.

Referring to FIG. 6, housing assembly 112 encloses an apparatus 133 for assembling a tip closure 15 onto a syringe barrels 12. The syringe barrels 12 which can be printed or unprinted, are essentially clean and are fed from a supply 130 to a recess 132 in a rotating table 134. The syringe barrels are made of glass or plastic and made by methods which produce clean and sterile devices. Table 134 rotates to station 135 where clean tip closures 15 are fed from a supply entrance 136 and coupled to the end of the syringe barrel 12 as shown in FIG. 1A. The table 134 continues to rotate to station 138 where the syringe barrel and tip closure assembly 137 is ejected onto a conveyor rail 140. Conveyor rail 140 is enclosed in a housing assembly 141 to maintain the same cleanliness levels as in housing assembly 112. Syringe barrel assemblies 137 are conveyed past nozzles 142 which directs streams of filtered, ionized air across the conveyor rail 140 to remove any particulates from the outer surface of syringe barrel assembly 137 and reduce static charge. Conveyor rail 140 has a discharge end 144 in housing assembly 114.

Housing assembly 114 contains a rotating table 146 having recesses 148 for receiving a syringe barrel assembly 137 from the conveyor rail 140. Table 146 rotates to carry the syringe barrel assembly 137 to a cleaning station 150 where streams of filtered, ionized air are directed into the syringe barrel assembly 137 to loosen and remove particulates from the inner surface while a vacuum is applied to the inner surface to carry the particulates away. Thereafter, table 146 rotates to carry the syringe barrel assembly 137 to a lubricating station 152 where a thin coating of a lubricant is applied to the inner surface of the syringe barrel assembly 137. The lubricant is preferably a silicone oil as known in the art. Table 146 then rotates to carry the syringe assembly 137 to a discharge station 154 where the syringe barrel assembly 137 is discharged onto a conveyor rail 156 to convey the syringe barrel assembly 137 to housing assembly 116.

In the embodiment illustrated, housing assembly 116 includes an access opening 129 in side wall 120 to enable an operator while sitting on a seat or chair 131 to reach into the housing assembly 116. The opening 129 is dimensioned to enable the operator to perform various manual operations while maintaining the workstation area at the desired cleanliness level. In the embodiment illustrated, the operator examines the syringe barrel assemblies 137 and places the assemblies in the tray 84 which is in the tub 92. The operator then places the protective sheet material 102 over the syringe barrel assemblies 137. The closure sheet 104 is then placed over the tub 92 and the tub is manually placed in housing assembly 118 through an opening 158 in side wall 120. In further embodiments, the syringe barrel assemblies 137 are placed in tub 92 automatically by suitable machinery.

Within housing assembly 118 is a heated platen 160 for heat sealing the closure sheet 104 onto tub 92. The platen 160 is lowered onto the sheet 104 and the sheet is fused to the flange 100 of the tub 92 to enclose the syringe barrel assemblies 137. At this time, the syringe barrel assemblies 137 are enclosed in a protective packaging so the tub can be removed from the housing assembly 118 without the risk of contamination of the syringe barrel assemblies 137. The tub is preferably sealed in a plastic bag or other protective outer wrap and placed in suitable shipping cartons. Standard heat sealing and bagging devices are typically used.

The tub package 82 can then be transferred to a suitable sterilization chamber 121. Sterilization can be, for example, by gamma or beta radiation, hot air or steam autoclave. In preferred embodiments, the cover sheet 104 is a gas permeable material which is permeable to ethylene oxide sterilizing gas. Typically, the tub package 82 is exposed to ethylene oxide for sufficient time to permeate the closure sheet and sterilize the contents thereof. The chamber is then evacuated and purged with carbon dioxide or other gas to remove the ethylene oxide.

In the embodiment illustrated in FIG. 6, sterilization chamber 121 is connected in line with housing assembly 118 to receive the tub package 82. In further embodiments, the tub packages 82 are heat sealed in a plastic bag or other protective wrap and transferred to a sterilization chamber at a different location. Sterilization can be after placing the packages 82 in suitable shipping cartons.

The apparatus of FIGS. 6–8 is intended to be exemplary of one embodiment of the invention. In this embodiment, the housing assemblies define different work stations and are in modular form for assembly and disassembly. In further embodiments, apparatus 110 can be a single housing enclosing each of the work stations.

Referring to FIG. 9, a flow chart depicts the method of assembly of the tub package 82. Clean syringe barrels are fed from a supply as indicated by block 170 and clean tip closures are fed from a supply as indicated by block 172 to a locally controlled environment for assembly of the tip closure to the syringe barrels indicated by block 174. The syringe barrel and tip closure assemblies are conveyed through a stream of clean, ionized air to remove particulates from the outer surface of the syringe barrel assemblies as indicated by block 176. The syringe barrel assemblies are then passed to a station where the inner surfaces of the syringe barrels are cleaned with filtered, ionized air and vacuum as indicated by block 178 and to a lubricating station where a lubricant is applied to the inner surface as indicated by block 180.

The lubricated syringe assemblies are placed in the tray and tub as indicated by block 182, followed by a protective sheet indicated by block 184 and outer cover sheet indicated by block 186. The tub package is placed in a heat sealer to seal the cover sheet to the tub indicated by block 188. The sealed tub is enclosed in a plastic bag indicated by block 190 followed by sterilization indicated by block 192.

Figure 10:
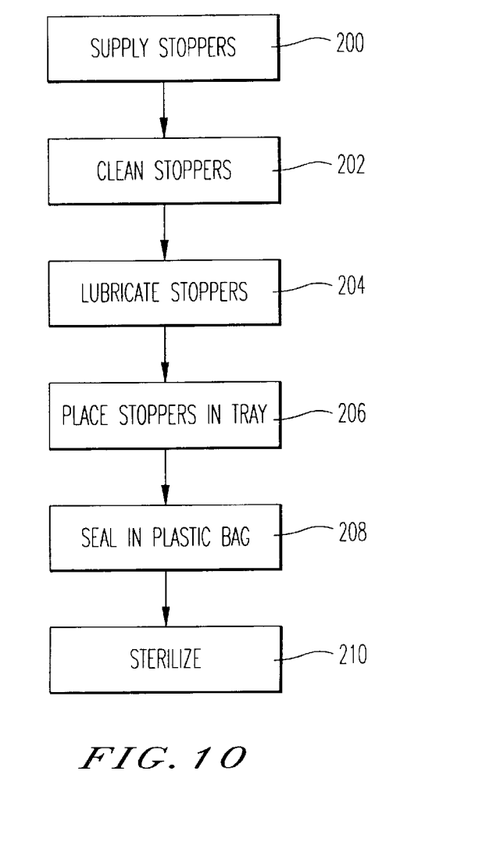
FIG. 10 is a schematic diagram of a flow chart of the packaging of syringe stoppers.

Referring to FIG. 10, a flow chart depicts the packaging steps for the stoppers 34. A plurality of stoppers are supplied as indicated by block 200, cleaned as indicated by block 202 and lubricated as indicated by block 204. The cleaned stoppers are placed in a tray indicated by block 206. The tray is sealed within a plastic bag indicated by block 208 and sterilized as indicated by block 210.

In a further embodiment, a housing assembly substantially as described above encloses a container filling device for filling the container with the desired substance. The container can be a suitable medical container, such as a vial or syringe barrel. The housing assembly includes an inlet receiving the container and an air or water wash device as needed. The filling device fills the clean containers and attaches a suitable closure to close the container. The cleaning, filling and assembling devices can be enclosed in a single housing assembly or enclosed in separate housing assemblies connected together in series by chutes, tunnels or other enclosures.

Figure 11:
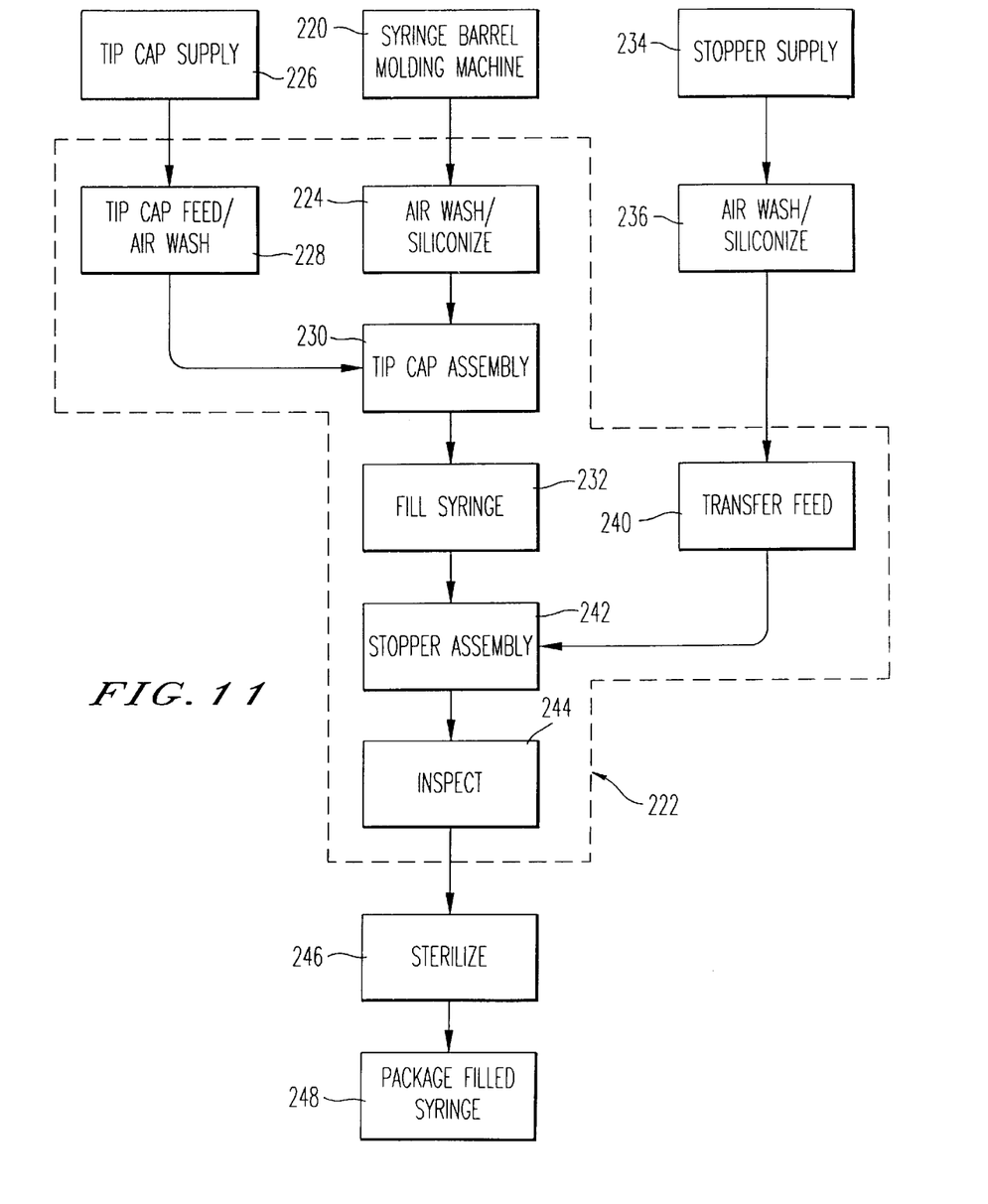
FIG. 11 is a schematic diagram of a flow chart of the syringe filling steps.

FIG. 11 illustrates a flow chart for a method of producing a prefilled syringe. Referring to FIG. 11, a supply of preformed syringe barrels are formed in a syringe barrel molding machine indicated by block 220. The molded syringe barrels are transferred into a locally controlled environment indicated by 222 preferably without any additional cleaning or sterilizing steps. It is preferred that the transferring of molded syringe barrels to the locally controlled environment be immediate. The syringe barrels are washed with air to remove particulates and coated with a lubricant such as silicone lubricating oil on the inner surface as indicated by block 224. A supply of tip caps indicated by block 226 is fed into the locally controlled environment 222. The tip caps are air washed as indicated by block 228. The cleaned tip caps and syringe barrels are conveyed to an assembly device indicated by block 230 where the tip caps are assembled onto the syringe barrel to close the tip or nozzle of the syringe barrel. The syringe barrel assemblies are then conveyed to a filing station indicate by block 232 where the syringe barrel is filled with a substance as defined herein.

A supply of stoppers indicated by block 234 is transferred to a washing station indicated by block 236 where a silicone lubricant is applied to the stoppers. The lubricated stoppers are then delivered to a transfer feed device indicated by block 240 within the locally controlled environment 222.

The stoppers are then assembled with the filled syringe barrels indicated by block 242 to close the syringe. In particular, the stopper is inserted into the open proximal receiving end of the syringe barrel. The prefilled syringes are preferably inspected for defects as indicated by block 244 and discharged form the locally controlled environment 222, sterilized as indicated by block 246 and packaged either individually or in bulk for transporting indicated by block 248. Suitable sterilization methods include heat, steam, radiation and gas sterilization as known in the art. In some uses, for example, if the syringe is to be used in a surgical procedure, the sterilization step should occur after the syringe is packaged. It is also within the purview of the present invention to include sterilization of the syringe both before and after packaging.

In the method of FIG. 11, the syringe barrels are breach filled and the tip cap is coupled to the barrel before filling. It will be understood by those skilled in the art that a stopper and/or syringe plunger can be coupled to the syringe barrel before filling and the syringe barrel filled through the tip or nozzle. Thereafter, a tip cap or needle can be attached to the filled syringe barrel to close the tip. Generally, the tip cap or needle is fed into the housing assembly and cleaned with an air stream before attaching to the syringe barrel nozzle. Accordingly, medical containers such as the syringe can be filled by known filling methods. Exemplary methods for filling syringes and other medical containers are disclosed in U.S. Pat. No. 5,620,425 to Hefferman et al., U.S. Pat. No. 5,597,530 to Smith et al., U.S. Pat. No. 5,537,042 to DeHaen, U.S. Pat. No. 5,531,255 to Vacca, U.S. Pat. Nos. 5,519,984 and 5,373,684 to Veussink et al., U.S. Pat. Nos. 5,256,154 and 5,287,983 to Liebert et al. and U.S. Pat. No. 4,718,463 to Jurgens, Jr. et al., which are hereby incorporated by reference in their entirety.

The locally controlled environment of the illustrated embodiments include assembly machinery for producing bulk packaging of syringe barrels and/or filling devices for producing prefilled syringes. It will be appreciated that other medical containers can be assembled, constructed or packaged in the locally controlled environment. Examples of containers which can be packaged including drug containers, vials, ampoules or other containers where a clean environment is required during the processing step. In addition, the cleanliness standard for the locally controlled environment is determined by the air filtration system to obtain a sufficient level as required. In the embodiment disclosed, the HEPA filters are sufficient to maintain a Class 100 cleanliness standard in each of the housing assemblies. In further embodiments, the HEPA filters can be selected to attain Class 10, Class 10,000 or Class 100,000 cleanliness conditions.

Although certain embodiments have been selected to illustrate the invention, it will be apparent to one skilled in the art that further embodiments can be obtained without departing from the scope of the invention. For example, processes within the scope of the invention can be used with either glass or plastic syringe barrels through changing of conditions to accommodate the requirements of glass or plastic while still following the process steps.

What is claimed is:

1. A method of producing a prefillable syringe barrel assembly comprising the steps of:

supplying a plurality of syringe barrels and a plurality of tip closures to at least one housing assembly having an air filtering device to maintain a predetermined cleanliness level, coupling said tip closures to said syringe barrels within said housing assembly to form syringe barrel assemblies, directing filtered air onto said syringe barrel assemblies to clean outer surfaces of said syringe barrel assemblies, directing filtered air to loosen particulates from inner surfaces of said syringe barrel assemblies and applying a vacuum to remove loosened particulates, and applying a lubricant to said inner surfaces of said syringe barrel assemblies, forming an array of said syringe barrel assemblies, and placing said array in a container having a closed bottom, side walls and an open top end applying a cover sheet to said container to entirely close said container, and sealing said cover sheet to said container, and placing said containers in another container and sealing said another container while in said housing assembly.

2. The method of claim 1, further comprising supplying a plurality of closures, filling each of said syringe barrel assemblies with a substance and closing said syringe barrel assemblies with said closures.

3. The method of claim 2, wherein said substance includes either water, saline solutions, flush solutions, contrast agents, pharmaceutical agents or vaccines.

4. The method of claim 2, wherein said substance is in either a dry state or a liquid state.

5. The method of claim 1, wherein said housing assembly maintains a cleanliness level of Class 100.

6. The method of claim 1, wherein said housing assembly includes an air blower and a HEPA filter coupled to said air blower to filter air entering said housing assembly.

7. The method of claim 6, further comprising the step of operating said air blower so as to maintain a positive pressure in said housing assembly.

8. The method of claim 1, further comprising a plurality of housing assemblies coupled together.

9. The method of claim 8, wherein said coupling step is in a first housing assembly, said cleaning and lubricating steps are in a second housing assembly, said step of forming an array and placing said array in a container is in a third housing assembly, and said sealing step is in a fourth housing assembly.

10. The method of claim 9, further comprising the step of positioning a protective sheet over said array of syringe barrel assemblies in said container before applying said cover sheet to said container.

11. The method of claim 10, wherein said cover sheet is a heat sealable sheet material and said method comprises heat sealing said cover sheet to said container to close said container.

12. The method of claim 9, further comprising the step of sterilizing said array of syringe barrel assemblies in said container after applying said cover sheet and an outer wrap.

13. The method of claim 12, wherein said sterilizing step comprising exposing said container to either gamma radiation, beta radiation, ethylene oxide, hot air, steam or a sterilizing gas.

14. The method of claim 12, wherein said cover sheet is a gas permeable sheet material and said sterilizing step comprises exposing said container to a sterilizing gas.

15. The method of claim 14, wherein said cover sheet is a sheet of spun bonded polyolefin.

16. The method of claim 1, wherein said container is a prefilled syringe, said method further comprising:

filling said syringe barrel assemblies with a substance, supplying a plurality of stoppers, and applying the stopper to each syringe barrel assembly to close said syringe barrel assembly.

17. The method of claim 16, further comprising applying a lubricant to inner surfaces of said syringe barrels.

18. The method of claim 1, wherein said syringe barrel is a plastic or glass syringe barrel.

19. The method of claim 1, further comprising the steps of supplying a plurality of collars and snapping the collar onto each syringe barrel prior to forming said array of said syringe barrel assemblies.

20. The method of claim 19, wherein said collar is a luer locking collar.

21. The method of claim 1, wherein said filtered air directed onto said syringe barrel assemblies to clean the outer surfaces of said syringe barrel assemblies is ionized air.

22. The method of claim 1, wherein said directed filtered air stream is ionized air.

23. A method of producing a prefilled medical container comprising the steps of:

supplying a plurality of medical containers to a first housing assembly having an air filtering device to maintain a predetermined cleanliness level, directing a filtered air stream to loosen particulates from inner surfaces of said medical containers and applying a vacuum to remove loosened particulates from said medical containers prior to filling, and filling said medical containers with a substance and closing said containers.

24. The method of claim 23, further comprising forming an array of said filled medical containers, and placing said array in a container package and closing said container package.

25. The method of claim 23, wherein said prefilled medical container is a plastic or glass syringe barrel.

26. The method of claim 25, further comprising the steps of:

supplying plurality of tip caps to said housing assembly, and coupling said tip caps to said syringe barrels before filling.

27. The method of claim 26, further comprising supplying a plurality of stoppers to assembly said housing and coupling said stoppers to said syringe barrels after filling.

28. The method of claim 26, further comprising the steps of supplying a plurality of collars and snapping the collar onto each syringe barrel prior to forming said array of said syringe barrel assemblies.

29. The method of claim 23, wherein said housing assembly includes an air blower and a HEPA filter coupled to said air blower to filter air entering said housing assembly to maintain a cleanliness level of Class 100.

30. The method of claim 29, further comprising the step of operating said air blower to maintain a positive pressure in said housing assembly.

31. The method of claim 23, further comprising the step of sterilizing said filled medical containers.

32. The method of claim 31, wherein said sterilizing step comprising exposing said filled medical containers to either gamma radiation, beta radiation, hot air, steam or a sterilizing gas.

33. A method of producing packaged prefillable syringe barrel assemblies comprising the steps of:

supplying a plurality of syringe barrels and a plurality of tip caps to a first housing assembly for maintaining a locally controlled environment, said first housing assembly having an air filtering device for introducing filtered air into said first housing assembly and maintaining a predetermined cleanliness level in said first housing assembly, coupling said tip caps to said syringe barrels to form syringe barrel assemblies, cleaning at least one surface of said syringe barrel assemblies, conveying said syringe barrel assemblies to a second housing assembly and applying a coating of a lubricant to inner surfaces of said syringe barrel assemblies in said second housing assembly, and forming an array of said syringe barrel assemblies, placing said array in a container, and closing and sealing said container to form said packaged refillable syringe barrel assemblies.

34. The method of claim 33, comprising conveying said lubricated syringe barrel assemblies to a third housing assembly and forming said array in said third housing assembly.

35. The method of claim 33, wherein said syringe barrels are plastic or glass prefillable syringe barrels.

36. The method of claim 33, wherein said first housing assembly includes an air blower and a HEPA filter coupled to said air blower to filter air entering said first housing assembly and to maintain a cleanliness level of Class 100.

37. The method of claim 36, further comprising the step of operating said air blower to maintain a positive pressure in said housing assembly.

38. The method of claim 33, further comprising the steps of supplying a plurality of collars and snapping the collar onto each syringe barrel prior to forming said array of said syringe barrel assemblies.

39. A method of producing packaged prefillable syringe barrel assemblies comprising the steps of:

supplying a plurality of syringe barrels and a plurality of tip caps to at least one housing assembly for maintaining a locally controlled environment, said at least one housing assembly having an air filtering device for introducing filtered air into said at least one housing assembly and maintaining a predetermined cleanliness level in said at least one housing assembly, coupling said tip caps to said syringe barrels to form syringe barrel assemblies, cleaning at least one surface of said syringe barrel assemblies, forming an array of said syringe barrel assemblies, placing said array in a container, positioning a protective sheet over said array of syringe barrel assemblies in said container and applying a cover sheet to said container and thereafter sealing said cover sheet to said container to form said packaged prefillable syringe barrel assemblies, said steps of coupling, cleaning, forming and sealing being carried out in said at least one housing assembly.

40. The method of claim 39, wherein said cover sheet is a heat sealable sheet material and said method further comprises heat sealing said cover sheet to said container to close said container.

41. The method of claim 39, further comprising the step of sterilizing said array of syringe barrel assemblies in said container after applying said cover sheet and an outer wrap.

42. The method of claim 41, wherein said sterilizing step comprises exposing said container to either gamma radiation, beta radiation, hot air, steam or a sterilizing gas.

43. The method of claim 39, further comprising the steps of supplying a plurality of collars and snapping the collar onto each syringe barrel prior to forming said array of said syringe barrel assemblies.

44. The method of claim 39, wherein the step of cleaning at least one surface of said syringe barrel assemblies includes directing ionized air to loosen particulates from said surface and applying a vacuum to remove loosened particulates from said syringe barrel assemblies.

* * * * *